(12) United States Patent
Otto et al.

(10) Patent No.: US 6,265,225 B1
(45) Date of Patent: *Jul. 24, 2001

(54) CAP FOR A REAGENT CONTAINER

(75) Inventors: Ralf Otto, Wiesbaden; Dieter Bickoni, Hochheim; Hugo Wilmes, Bad Soden, all of (DE)

(73) Assignee: Dade Behring Marburg GmbH, Marburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/172,852

(22) Filed: Oct. 15, 1998

(30) Foreign Application Priority Data

Oct. 18, 1997 (DE) ................................. 197 46 169

(51) Int. Cl.⁷ ........................ G01N 35/00; B65D 43/02
(52) U.S. Cl. ................... 436/180; 422/104; 422/102; 215/236; 220/816
(58) Field of Search .................... 422/102, 104; 215/236; 220/812, 816, 820, 824; 436/180

(56) References Cited

U.S. PATENT DOCUMENTS

| | | | |
|---|---|---|---|
| 1,090,883 | * | 3/1914 | Schott ................................ 220/816 |
| 1,314,306 | * | 8/1919 | Cullison ............................. 220/816 |
| 1,998,373 | * | 4/1935 | Love .................................. 220/820 |
| 2,030,380 | * | 2/1936 | Love .................................. 220/820 |
| 2,583,085 | * | 1/1952 | Campbell ........................... 220/816 |
| 5,271,897 | * | 12/1993 | Wurschum et al. ................. 422/63 |

FOREIGN PATENT DOCUMENTS

| | | |
|---|---|---|
| 3346517A1 | 8/1984 | (DE) . |
| 0509281A2 | 10/1992 | (DE) . |
| 35 04258 A1 | 8/1996 | (DE) . |
| 0 331 057 A2 | 9/1989 | (EP) . |
| 0543638A1 | 5/1993 | (EP) . |
| WO 95/04685 | 2/1995 | (WO) . |
| WO 96/35621 | 11/1996 | (WO) . |

* cited by examiner

Primary Examiner—Robert J. Warden, Sr.
Assistant Examiner—Kaj K. Olsen
(74) Attorney, Agent, or Firm—Finnegan, Henderson, Farabow, Garrett and Dunner, L.L.P.

(57) ABSTRACT

A description is given of a cap for a reagent container having a sealable lid, where the lid
- can be pivoted laterally upward from the cap sealing position, with the container being opened, by means of an inclined bistable hinge,
- bears one or more catches which can come into contact with an apparatus for opening or closing the lid, and the cap has one or more centering elements by means of which the reagent-container setting position in the analyzer is fixed.

12 Claims, 2 Drawing Sheets

CAP FOR A REAGENT CONTAINER

Figure 1:
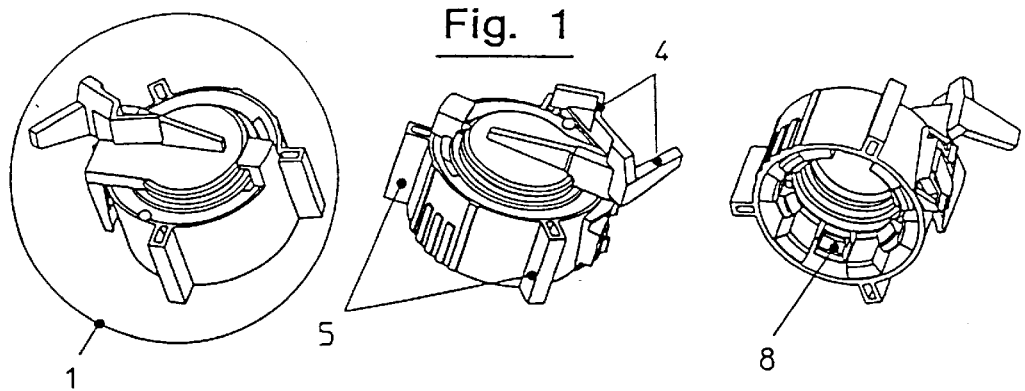

The invention relates to a cap for a reagent container, which cap is provided with a sealable lid.

Various embodiments for sealing reagent containers have already been developed, by which the evaporation and contamination of reagents which are used for the analysis of biological fluids are to be decreased. DE-A 33 46 517 has already disclosed an opening and closing apparatus for a reagent container which is to prevent evaporation of the fluid. A lid is provided for this, which has a multiplicity of elevations of elastic material on its underside. This lid is mounted onto the reagent container in an airtight manner by a closing mechanism, and it may also still be readily removed from the container when the container contents are frozen.

EP-A-0 509 281 discloses a container closure having a puncturable closure body which permits the removal or addition of fluids by means of a blunt hollow needle, the container closure consisting at least in part of a highly elastic material which is cut into by at least 75% of its thickness at the point of puncture. The closure in this case can be implemented on its own in the form of a stopper or as an insert disk for a closure. However, in this case, there is the risk that the hollow needle becomes contaminated on puncturing the container closure.

Furthermore, EP 0 543 638 discloses a closure which is mounted so as to be able to pivot on an extended arm and, in a first position, seals the orifice of the vessel, and in a second position, does not seal the orifice. In this case the extended arm is provided with a pretensioning apparatus which ensures the sealing of the reagent container.

The object underlying the abovementioned closures is to protect the test samples and reagents from contamination and evaporation. In particular, the reagents which are used for program-controlled analysis of a biological fluid in an analyzer, and from which small amounts of reagent are continually removed over a relatively long period by means of a pipette, must be kept hermetically sealed before, during and after the pipetting and this seal must be ensured even after multiple use. These requirements have not yet been satisfactorily solved by the sealing apparatuses developed hitherto, because the risk of unwanted carry-over of traces of the reagent or of the biological fluid from one vessel to another has not been reliably excluded and adequate protection against evaporation was not provided.

The object was therefore to develop an improved closure for reagent containers which are used in program-controlled analyzers and must remain reliably and hygienically sealed even in the event of multiple use. At the same time, the closure should be as similar as possible in its external dimensions to the closures known and used hitherto, so that the analytical instruments which are already in existence do not have to be modified. Moreover, for a program-controlled analyzer, it is also necessary that it can recognize each reagent vial on the basis of the barcode applied to the exterior in order to be able to select the reagent necessary for a defined determination. However, that is only possible if the reagent is centered in a previously established position in the analyzer, because only then does the barcode become visible at the position recognizable for the automatic reading device.

These objects are achieved by a cap for a reagent container, which cap is provided with a sealable lid which
  a) can be pivoted laterally upward from the cap sealing position, with the container being opened, by means of an inclined bistable hinge,
  b) bears one or more catches which can come into contact with an apparatus for opening or closing the lid, and the cap has one or more centering elements by means of which the reagent-container setting position in the analyzer is fixed.

Figure 2:
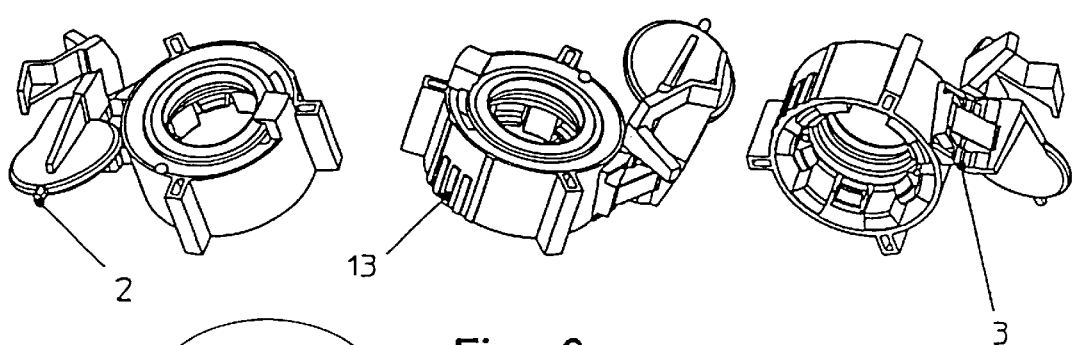
Figure 3:
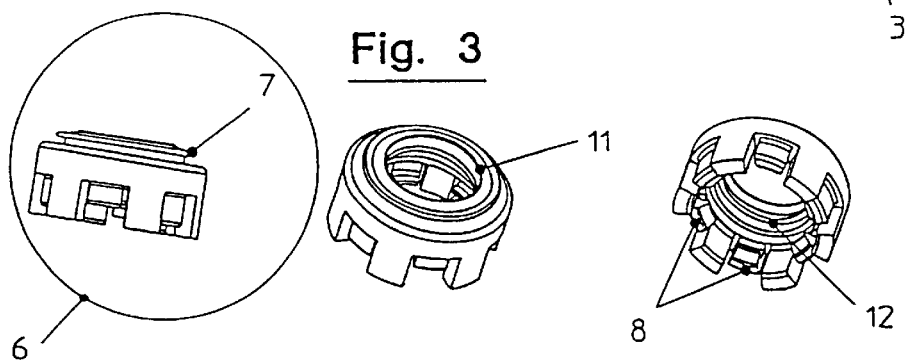
Figure 4:
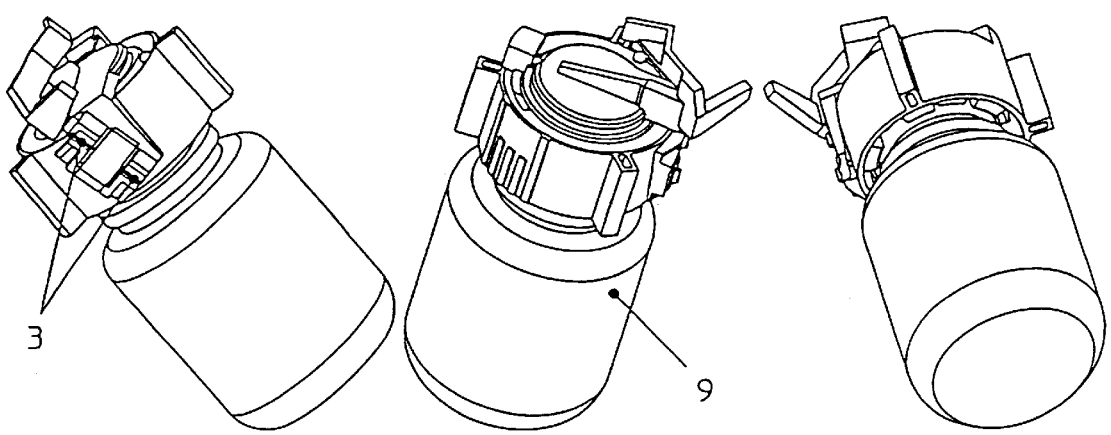
Figure 5:
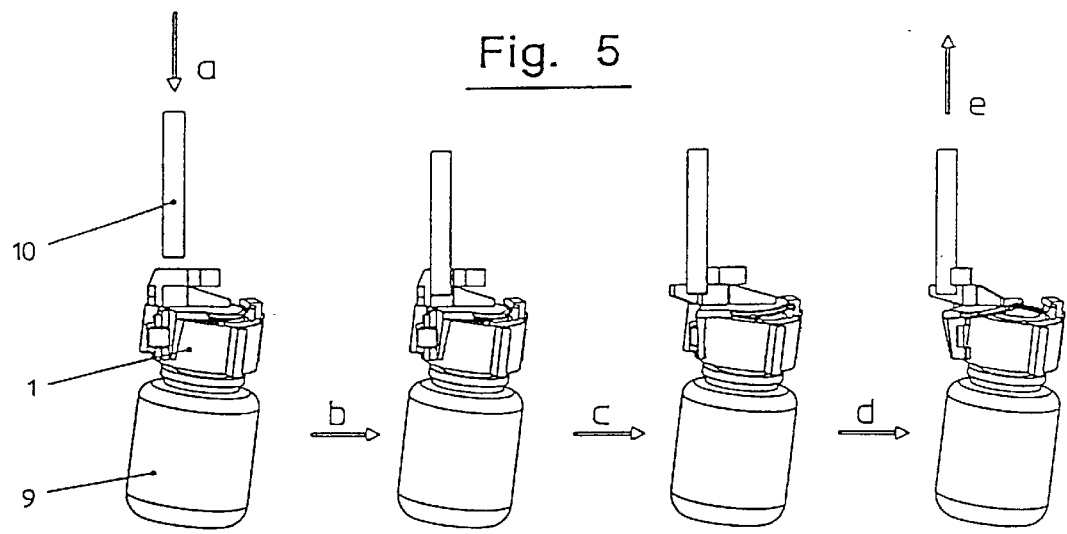
Figure 5:
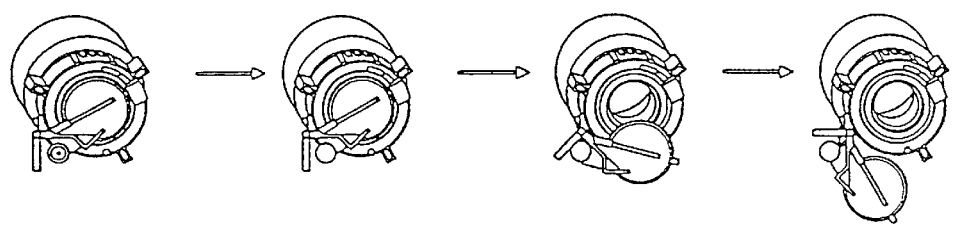
Figure 6:
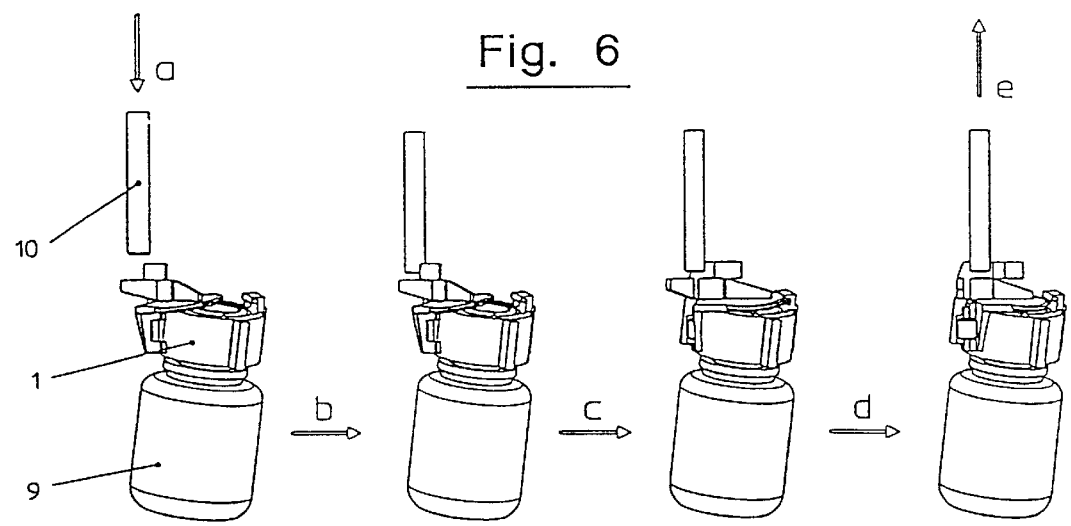
Figure 6:
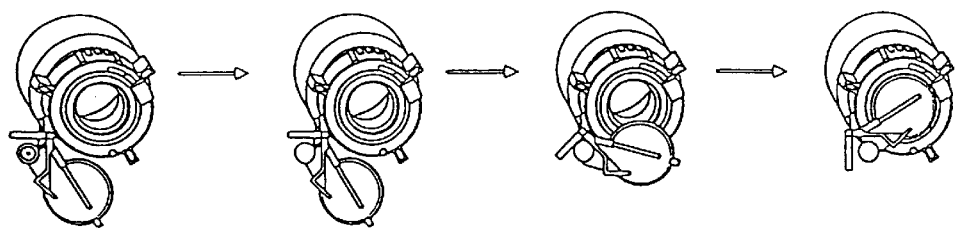

FIG. 1 shows the cap according to the invention, with lid closed, from various points of view, FIG. 2 shows the cap with lid open, FIG. 3 shows the sealing insert provided for the cap, FIG. 4 shows a reagent container together with the cap according to the invention, FIG. 5 shows various positions of the lid during the opening of the cap FIG. 6 shows various positions of the lid during the closing of the cap.

The lid of the cap according to the invention (FIGS. 5 and 6) is opened and closed by a ram 10 moving in a vertical direction which engages with the catches 4 mounted on the cap according to the invention and automatically opens the lid 2 as soon as the reagent container 9 reaches in the analyzer the position intended for removal of the reagent fluid.

As shown in FIG. 5, the ram 10 in process step a falls vertically downward, entering into contact with the catch mounted on the cap 1. During the automatic further transport of the reagent container 9 in the analyzer, the lid is completely opened in process steps b to d and the ram is then raised again in process step e. The reagent fluid can then be removed by a pipette which is not shown.

FIG. 5 likewise shows, in plan view from above, the various positions of the lid to the cap during the opening process. After the removal of the reagent fluid, the further movement of the reagent container 9 in the analyzer leads to renewed contact of the ram 10 with a catch 4 mounted on the lid, which causes closing of the lid.

FIG. 6 correspondingly shows the closing operation in a plurality of sequential steps. The inclined position of the bistable hinge 3 joined to the lid causes the lid to be slightly raised during opening and to be lowered onto the cap during closing. The time the reagent vessel is open is thus only dependent on the time required to remove the reagent fluid. As soon as the reagent container is taken away again from the removal position, the lid of the vessel seals owing to the action of the ram 10 on the catch 4 of the lid.

A particularly tight seal of the lid may be achieved if a lug is mounted on the lid, which lug engages into a recess in the cap sealing position and as a result ensures compressively loaded sealing between the lid and the upper rim of the cap.

For reliable sealing of the cap 1 against the reagent container 9, according to the invention, an inner seal insert 6 consisting of an elastic material is used, which insert is shown in FIG. 3. It features the fact that it is fastened in the cap by a retaining bead 7 encompassing the seating surface of the lid and bears sealing lips between cap and lid 11 and between cap and container orifice 12. In addition, the seal insert has, in the interior of the cap, structures 8 which ensure the free rotatability of the cap on the reagent container and ensure the sealing of differently shaped container orifices.

The free rotatability of the reagent container with the cap stationary without losing tightness of seal is necessary because the reagent container must assume a precisely predetermined position in the analyzer. That is to say, the container must be orientated in such a manner that its barcode can be detected by a reading instrument which recognizes the contents of the reagent container on the basis of the barcode and is thus able to steer the reagent required for the particular analysis into the appropriate removal position. To facilitate the precise positioning of the reagent container into the barcode position recognizable by the reading instrument, a marking 13 can be applied on the cap according to the invention, which marking indicates the position which the barcode must assume in relation to the cap.

The position of the reagent container in the analyzer is, moreover, also established by one or more centering elements 5 which are mounted on the cap according to the invention and ensure that the reagent vessel can only be inserted into the analyzer in an accurately determined position. The centering elements, moreover, have the object of preventing a change in the position of the reagent container during the automatic opening and closing of the lid by the ram 10.

The reliability of the analytical results can also be increased still further visually by means of the cap according to the invention by the reagents necessary for a certain determination being provided with caps of the same color.

FIG. 4 shows the glass reagent container together with the cap according to the invention. Whereas the cap can consist of one or more different plastics, the reagent container itself preferably consists of a transparent plastic or glass. It is particularly advantageous that reagent vessels of differing shape can be sealed with the same cap according to the invention and can thus be used in an automatic analyzer.

The cap according to the invention makes a considerable contribution to ensuring uniformly reliable analytical results. By preventing the evaporation of the solvent of the reagents, the concentration of the reagents remains constant. Contamination of the reagent solutions and biological fluids is reliably prevented by the pipettes used in the process according to the invention being brought, after each operation, to a washing apparatus and there freed from all adhering constituents.

List of Reference Numbers:

1 cap
2 lid
3 bistable hinge
4 catch
5 centering element
6 seal insert
7 retaining bead
8 structures on the seal element
9 reagent container
10 ram
11 upper sealing lip
12 inner sealing lip
13 marking for barcode

What is claimed is:

1. A cap for a reagent container provided with a sealable lid that can be pivoted axially and transversely by an inclined bistable hinge bearing one or more catches when the one or more catches come into contact with a transverse force, the cap being freely rotatable with respect to the reagent container when sealingly connected to the reagent container.

2. The cap as claimed in claim 1, wherein the lid can be opened and closed by a mechanically actuated apparatus.

3. The cap as claimed in claim 1, wherein the lid bears a lug which engages into a recess when the cap is in a cap sealing position and as a result ensures compressively load sealing between the lid and an upper rim of the cap.

4. The cap as claimed in claim 1, wherein the cap further comprises an inner seal insert comprising an elastic material.

5. The cap as claimed in claim 4, wherein the seal insert has structures on the interior of the seal insert which are capable of sealing an orifice of a reagent container and which are capable of allowing the rotatability of the cap on the reagent container while also being capable of sealing differently shaped container orifices.

6. The cap as claimed in claim 1, wherein the lid is held stable in an open position or a closed position by the inclined bistable hinge.

7. The cap as claimed in claim 1, wherein it bears a marking which allows a previously established defined orientation of the cap to a reagent container.

8. The cap as claimed in claim 1, having a color indicative of the reagent.

9. The cap as claimed in claim 1, comprising one or more thermoplastics.

10. A process for program-controlled analysis of a biological fluid in an analyzer in which a sample of the fluid is brought together with one or more detection reagents in a measuring vessel, wherein the detection reagents are removed from a container by a pipette, which container bears a cap as claimed in claim 1, and the pipette is cleaned in a wash station after each removal operation.

11. The cap of claim 1 further comprising one or more centering elements capable of being held by a machine to substantially fix the transverse and axial position of the cap to a setting position.

12. A cap for a reagent container provided with a sealable lid that can be pivoted axially and transversely by an inclined bistable hinge bearing one or more catches when the one or more catches come into contact with a transverse force, and an inner seal insert comprising an elastic material, the seal insert having contours, by which it is held axially in the cap, and has sealing lips between the cap and the lid and between the cap and an orifice of a reagent container.

* * * * *